United States Patent [19]

Woog

[11] Patent Number: 5,071,348

[45] Date of Patent: Dec. 10, 1991

[54] BRUSH AND MASSEUR FOR INTERPROXIMAL DENTAL CLEANING

[75] Inventor: Philippe-Guy E. Woog, Vesenaz, Switzerland

[73] Assignee: Les Produits Associates LPA-Broxo S.A., Geneva, Switzerland

[21] Appl. No.: 617,924

[22] Filed: Nov. 21, 1990

Related U.S. Application Data

[63] Continuation of Ser. No. 935,712, Nov. 28, 1986, abandoned.

[51] Int. Cl.$^5$ .............................................. A61C 3/03
[52] U.S. Cl. ................................... 433/118; 433/125; 132/308; 128/62 A
[58] Field of Search ............... 433/125, 130, 142, 118; 15/167 R, 22 R; 132/308, 309, 310; 128/62 A, 66

[56] References Cited

U.S. PATENT DOCUMENTS

| | | | |
|---|---|---|---|
| 2,016,597 | 10/1935 | Drake | 433/142 |
| 2,800,899 | 7/1957 | Barron | 128/62 A |
| 2,911,660 | 11/1959 | Klemas et al. | 128/62 A |
| 3,204,275 | 9/1965 | Baker | 15/167 R |
| 3,802,420 | 4/1974 | Moffat et al. | 128/62 A |
| 3,978,852 | 9/1976 | Annoni | 128/62 A |
| 3,987,549 | 10/1976 | Robertelli | 433/125 |
| 4,257,433 | 3/1981 | Kwan | 128/66 |
| 4,397,055 | 8/1983 | Cuchiara | 15/22 R |
| 4,572,223 | 2/1986 | Rosenfeld | 15/167 R |
| 4,576,190 | 3/1986 | Youssef | 15/167 R |

FOREIGN PATENT DOCUMENTS 2949647 6/1981 Fed. Rep. of Germany ...... 433/125
1766651 12/1981 Fed. Rep. of Germany ...... 433/142

Primary Examiner—John J. Wilson
Attorney, Agent, or Firm—Kane, Dalsimer, Sullivan, Kurucz, Levy, Eisele and Richard

[57] ABSTRACT

A tooth brush apparatus capable of cleaning and massaging the interproximal dental areas. The apparatus is used in conjunction with a motor driven tooth brush handle and is inserted into the areas between the teeth during use.

7 Claims, 2 Drawing Sheets

BRUSH AND MASSEUR FOR INTERPROXIMAL DENTAL CLEANING

This is a continuation of copending application Ser. No. 06/935,712, filed on Nov. 28, 1986, now abandoned.

FIELD OF THE INVENTION

The present invention relates to motor-driven tooth cleaning devices and more particularly is related to replaceable brush and tip components.

BACKGROUND OF THE INVENTION

Interproximal stimulation long has been recommended in a total periodontal regimen because such stimulation 1) provides greater blood flow to an area which, because of its protected placement, does not permit the stimulatory effect provided by the normal masticatory process and 2) provides greater flow of crevicular fluid which helps cleanse the area and provides prostaglandins, polymorphonuclear leukocytes and immunoglobulins to provide a line of defense against bacteria and other deleterious agents.

The suggestions in the past have been to place wood, rubber or other substances, provided in a conical shape, into the interproximal areas and rather vigorously move them from side to side. This was to be done with enough vigor to provide the necessary stimulation *but* short of a force which would cause harm to these tissues.

Presently, a mechanical device is marketed which reputedly can provide the required stimulatory effect. This device, however provides rotary movement in only *one* direction thereby producing stimulation of an unequal force. This unidirectional rotary action actually causes a tickling sensation. This device also provides an action which could be too vigorous for the tissue especially if inflammation is present in the gingival tissue *and* the existence of inflammation in the gingivae is one of the reasons interdental stimulation is recommended.

Electric tooth brushes that are currently available employ either an oscillating or a rotating brush. The oscillating brushes effectively clean the flat surfaces of the teeth and give a physiologic massage to the gums to remedy lack of biting hard food. They are somehow less effective at removing plaque which collect on the interproximal surfaces of the teeth. The inorganic matter left in these areas will cause decay and gingiovitis.

The rotating brushes to date produce a tickling sensation and have proven less effective at cleaning the flat dental surfaces. Furthermore these tips however are sometimes shielded or are too large to clean the interproximal surfaces of the tooth. The shields are provided to protect the brush from scraping the inside of the cheek, tongue, or sensitive gum areas during the brushing operation. As such the shields prohibit using the end of the brush to clean the interproximal areas.

Furthermore the brushes are large so that when the bristles brush across the teeth, they sweep into the spaces between the teeth and hopefully remove the organic matter. Because of their size these brushes can not be used to clean all the interproximal areas thoroughly. The brush is too large to allow it to be maneuvered into some of the tighter areas of the mouth.

The sweeping of the bristles across the surface of the various crevices in the mouth does not permit the proper penetration needed for a thorough cleaning. Permanent dental prosthesis such as bridgework or procelain caps which require thorough cleaning, add to the ineffectiveness of the prior art devices.

SUMMARY OF THE INVENTION

The present invention is an interproximal brush and or soft conical shaped tip designed for removing food particles and other organic matter from the interproximal surfaces of the tooth.

A further object of the invention is to provide a tip in the form of a removable brush which enters into crevices within the mouth instead of merely sweeping across its surface.

An additional object of the invention is to massage gums and remove dental plaque from surfaces of teeth and provide an interproximal cleaning device which is easy to use and is simple in construction and operation and capable of easy manufacture at relatively small cost.

The interproximal stimulator of the present invention also provides:

1) A oscillating reciprocating motion which is more physiologically acceptable to the tissue; i.e., it provides equal stimulation forward and backward which produces a more equalized blood vessel stimulation as well as increased crevicular fluid flow (with the associated polymorphonuclear leukocytes, prostaglandins and immunoglobulins) in the sulcus (crevice) of the tooth distal to where the stimulation is being applied as well as to that of the mesial tooth.

2) Stimulation at a level of vigor, speed and angle which should not be deleterious to the interdental tissue even at maximal torque and angle.

3) The ability to change simultaneously both angle and torque, according to gums sensitivity. This is important because it assures that a damaging pressure will not be applied to the sensitive tissues which have the may be most severely damaged if subjected to too great a force.

BRIEF DESCRIPTION OF THE DRAWINGS

In the drawings in which like reference numerals indicate corresponding parts throughout the several views.

DETAILED DESCRIPTION OF THE PREFERRED EMBODIMENT

Figure 1:
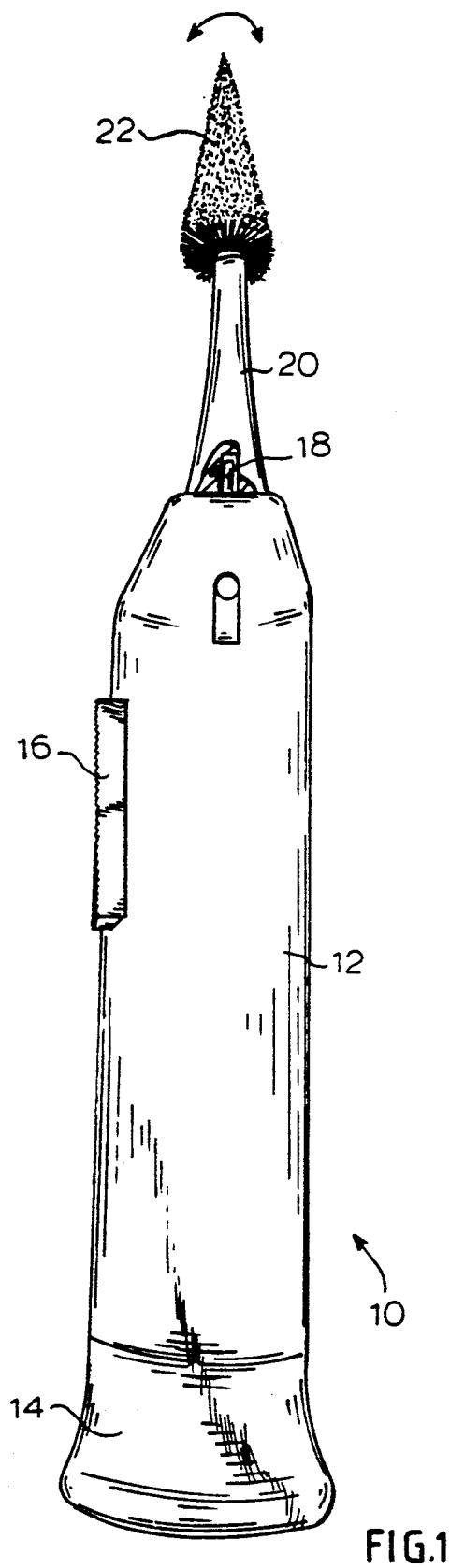
FIG. 1 is a side elevational view of a reciprocal motor driven removal conical tooth brush.
Figure 2A:
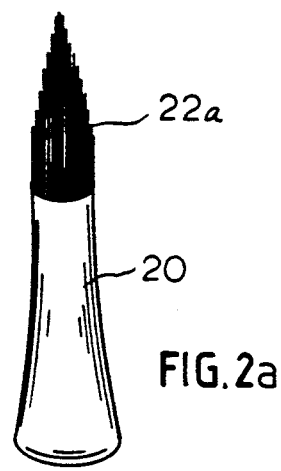
FIG. 2a shows another form of brush, with bristles extending axially.
Figure 2B:
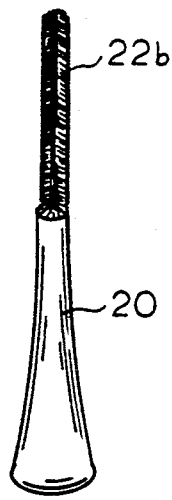
FIG. 2b shows still another form of brush that is elongated.
Figure 2C:
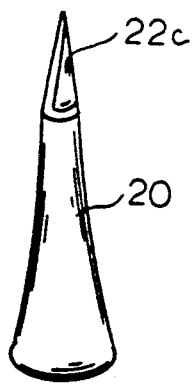
FIG. 2c shows a plastic or stimulator.
Figure 3:
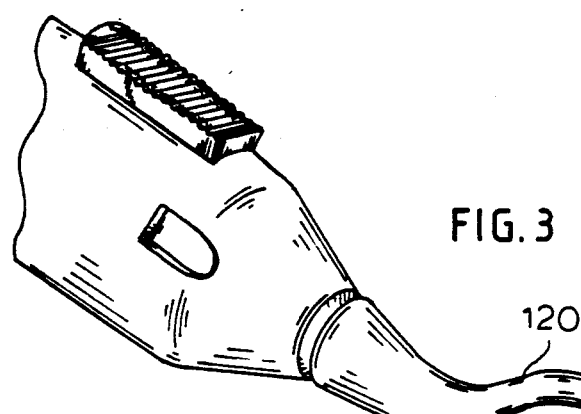
FIG. 3 is a fragmentary perspective view of a power handle with a reversible removable arm that permits the interdental brush and gingival stimulator to be placed in two operating positions to work on the teeth and gums from the front or rear.
Figure 4:
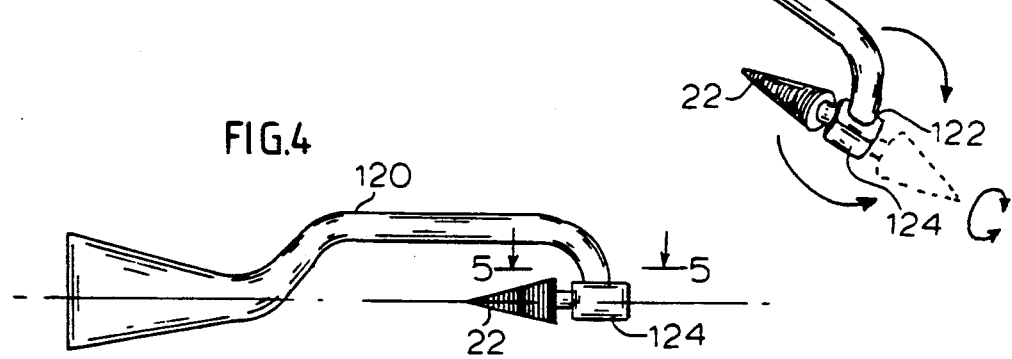
FIG. 4 is a side elevational view of the arm and brush.
Figure 5:
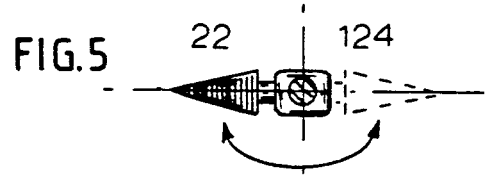
FIG. 5 is a top plan view with a section taken along line 5.5 of FIG. 4.

Referring now to FIG. 1 there is shown an electric tooth brush generally indicated by reference character 10. The electric toothbrush is generally comprised of a handle portion 12, with a base 14 housing an electrically reversible motor (not shown) operated by means of switch 16. The motor may be operated by means of a cord plugged into a regular electrical outlet, by batteries or by a rechargeable cell.

The electric toothbrush is provided with a reciprocal motor driven rod 18 adapted to connect detachably with the stem or arm 20 for a detachable and removable conical rotary brush 22 which is adapted to rotate inside the mouth in a reciprocal fashion during use. The brush being reciprocally rotatable provides optimum cleaning and stimulating action Towards this end, the brush oscillates back and forth at a predetermined frequency and between a predetermined angle about an axis coaxial with the axis of stem 20.

The brush 22 is easily detachable, removable and replaceable, and during a single cleaning of the mouth it is expected that more than one form of brush may be used. The conical brush 22 possesses radial bristles and is used effectively for cleaning and massaging the area between the teeth just above the gum line. In this connection, the brushes of this invention are extremely small in size to be readily inserted generally into small spaces as is normally the case between teeth above the gum line. Food particles and plaque often collect in this area. Brush 22a with coaxial bristles is designed to remove plaque around the gum line. Brush 22b also with lateral bristles is effective in cleaning spaces between teeth. The plastic stimulator tip 22c is mostly used for massaging and stimulating gums. The brushes 22, 22a and 22b and tip 22c may be used for maneuvering into less accessible areas and for children and smaller mouths.

Figure 6:
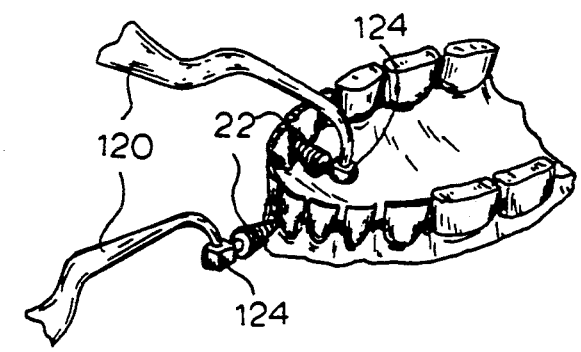
FIG. 6 is a perspective view of the reversible brush action in the front and rear of the teeth and gums.

In FIGS. 3–6 a two position interdental arm 120 is shown which is detachable, mounted and reciprocally driven on the power handle bands 12. The free end 122 of the arm 120 is adapted to receive any one of the bracket 124 which may be turned or rotated 180° C. and latched in one of two coaxial positions by any one of many common latching mechanism (not shown) as for example, a ball and detent assembly. In one coaxial position the brush extends away from the base of the arm and in the other position towards the base of the arm as depicted in FIG. 6. As is clearly shown the brush 22 may advantageously work on the front and rear of the teeth by placing bracket 124 in one of its two positions.

What is claimed is:

1. A tooth brush assembly capable of cleaning and massaging the interproximal dental areas, which comprises:
   a motor driven tooth brush handle which includes an output drive and means for rotationally oscillating said output drive;
   an arm detachably connected to said output drive of said handle; and
   a relatively small rotationally symmetric brush detachably connected to said arm and so constructed and arranged to be inserted into said interproximal areas of the teeth during use, wherein the arm and consequently the brush rotationally oscillate about an axis coaxial with said output drive of said handle to facilitate the cleaning and massaging operation, the rotational oscillation of the brush being physiologically acceptable to the tissue of the gums and provides relatively equal stimulation in one direction and a reverse direction which produces a more equalized blood vessel stimulation as well as increased crevicular fluid flow in the sulcus of the tooth distal to where the stimulation is being applied as well as that of the mesial tooth, the angle and torque of the rotatably oscillating brush being capable of being changed simultaneously according to gum sensitivity so that the stimulation is not deleterious to the interdental tissue even at maximum torque and angle.

2. The tooth brush assembly of claim 1 wherein said brush has bristles laterally arranged and so shaped to allow said brush to penetrate said interproximal areas.

3. The brush assembly of claim 2 wherein the brush is conical in shape.

4. The brush assembly of claim 2 wherein the bristles possess about the same length.

5. A tooth brush assembly capable of cleaning and massaging the interproximal dental areas, which comprises:
   a motor driven tooth brush handle which includes an output drive and means for rotationally oscillating said output drive;
   an arm detachably connected to said output drive of said handle; and
   a relatively small brush detachable connected to said arm and so constructed and arranged to be inserted into said interproximal areas of the teeth during use, wherein the arm and consequently the brush rotationally oscillate about an axis coaxial with said output drive of said handle to facilitate the cleaning and massaging operation, the brush having bristles extending coaxially and forming a conical tip.

6. A tooth brush assembly capable of cleaning and massaging the interproximal dental areas which comprises:
   a motor driven tooth brush handle which includes an output drive and means for rotationally oscillating said output drive;
   an arm detachably connected to said output drive of said handle; and
   a relatively small brush detachably connected to said arm and so constructed and arranged to be inserted into said interproximal areas of the teeth during use, wherein the arm and consequently the brush rotationally oscillate about an axis coaxial with said output drive of said handle to facilitate the cleaning and massaging operation, the brush being a soft plastic conically shaped tip which inserts into said interproximal areas during use, said tip being in the form of a pyramid with the apex of the pyramid lying substantially on the longitudinal axis of said shaft.

7. A tooth brush assembly capable of cleaning and massaging the interproximal dental areas which comprises:
   a motor driven tooth brush handle which includes an output drive and means for rotationally oscillating said output drive;
   an arm detachably connected to said output drive of said handle; and
   a relatively small brush detachably connected to said arm and so constructed and arranged to be inserted into said interproximal areas of the teeth during use, wherein the arm and consequently the brush rotationally oscillate about an axis coaxial with said output drive of said handle to facilitate the cleaning and massaging operation, the arm including a free end and means at the free end to position the brush in one position extending axially away from said handle and in another position extending axially towards said handle to permit cleaning of the teeth respectively from the front and rear.

* * * * *